United States Patent
Sakamoto et al.

(10) Patent No.: US 10,463,581 B2
(45) Date of Patent: Nov. 5, 2019

(54) SEALER COMPOSITION FOR ROOT CANAL FILLING

(71) Applicant: SHOFU INC., Kyoto (JP)

(72) Inventors: Shuji Sakamoto, Kyoto (JP); Katsuya Kimoto, Kyoto (JP); Toshiyuki Nakatsuka, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 15/432,004

(22) Filed: Feb. 14, 2017

(65) Prior Publication Data

US 2017/0231874 A1    Aug. 17, 2017

(30) Foreign Application Priority Data

Feb. 15, 2016   (JP) .................. 2016-025497

(51) Int. Cl.
*A61K 6/083*    (2006.01)
*A61K 6/00*    (2006.01)

(52) U.S. Cl.
CPC .......... *A61K 6/0835* (2013.01); *A61K 6/0038* (2013.01); *A61K 6/0073* (2013.01); *A61K 6/0091* (2013.01)

(58) Field of Classification Search
None
See application file for complete search history.

(56) References Cited

U.S. PATENT DOCUMENTS

| | | | | |
|---|---|---|---|---|
| 5,411,584 A | * | 5/1995 | Akinmade | A61K 6/0835 106/35 |
| 6,264,472 B1 | * | 7/2001 | Okada | A61K 6/0017 433/228.1 |
| 2002/0088372 A1 | * | 7/2002 | Abiru | A61K 6/0038 106/35 |
| 2003/0136303 A1 | * | 7/2003 | Kobayashi | A61K 6/0835 106/35 |
| 2005/0261393 A1 | * | 11/2005 | Mikulla | A61K 6/0835 523/113 |
| 2010/0068678 A1 | * | 3/2010 | Tanaka | A61K 6/0038 433/224 |
| 2017/0165034 A1 | * | 6/2017 | Engqvist | A61K 6/0835 |

FOREIGN PATENT DOCUMENTS

| | | |
|---|---|---|
| CA | 1299311 | 4/1992 |
| GB | 2 291 060 | 1/1996 |
| JP | 60-181004 | 9/1985 |
| JP | 62-19508 | 1/1987 |
| JP | 02-250811 | 10/1990 |
| JP | 2002-220314 | 8/2002 |
| JP | 3638615 | 4/2005 |

OTHER PUBLICATIONS

Neutralizing Carbopol and Pemulen Polymer in Aqueous and Hydroalcoholic Systems, Lubrizol (Year: 2009).*
Extended European Search Report dated Jun. 29, 2017 in European Application No. 17156050.1.

* cited by examiner

*Primary Examiner* — Peter A Salamon
(74) *Attorney, Agent, or Firm* — Wenderoth, Lind & Ponack, L.L.P.

(57) ABSTRACT

To provide a sealer composition for root canal filling consisting of a liquid material containing a polymer (a) of an acid group-containing polymerizable monomer in which a portion or the entirety of the acidic group in a molecule forms a salt with an alkaline metal and water (b), wherein the pH of the liquid material is in the range from 3.5 to 5.5, and a powder material containing an acid reactive inorganic powder (c), wherein, a cured product of a kneaded material of the liquid material and the powder material comprises 3 to 20 part by weight of the polymer (a), 10 to 60 part by weight of the water (b), and 30 to 85 part by weight of the acid reactive inorganic powder (c).

4 Claims, No Drawings

SEALER COMPOSITION FOR ROOT CANAL FILLING

This application is based on and claims the benefit of priority from Japanese Patent Application Serial No. 2016-025497 (filed on Feb. 15, 2016), the contents of which are hereby incorporated by reference in their entirety.

BACKGROUND OF THE INVENTION

Field of the Invention

The present disclosure relates to a sealer composition for root canal filling for filling a root canal after pulpectomy or after treatment for an infection root canal to prevent invasion of bacteria into the root canal. More specifically, the present disclosure relates to a sealer composition for root canal filling which has a hydrophilic property, good wettability to a tooth substance, a low unpleasant odor, a low irritation, a low harmful action, an excellent biocompatibility, a sufficient operation surplus time suitable for root canal filling, and excellent dimensional stability after curing, and wherein a cured product of the sealer composition for root canal filling can be easily removed without damaging the tooth substance when it becomes necessary to remove the cured product after surgery.

Description of the Related Art

In an endodontic procedure, a root canal filling has been performed in order to prevent invasion of bacteria into the root canal and to prevent infection after pulpectomy or after treatment for an infection root canal. In a general technique of the root canal filling, a root canal is sealed by using a gutta-percha point consisting of a gutta-percha and zinc oxide, and a sealer for root canal filling, at the same time. Requirements for a sealer for root canal filling include an excellent biocompatibility such as good wettability or adhesion to the root canal tooth containing a large amount of water and a low harmful action to an apical periodontal tissue, fluidity suitable for root canal filling, a sufficient operation surplus time suitable for root canal filling, little shrinkage at the time of curing, excellent dimensional stability after curing, a high X-ray contrast property, excellent removability of a cured product in re-treatment of a root canal, and the like. Furthermore, it takes particularly a long time to treat in a treatment for a tooth having a plurality of root canals. Therefore, a low odor is also required because a burden is imposed on the patient when there is an unpleasant odor in a sealer for root canal filling.

On the other hand, various sealers for root canal filling have been proposed so far, but each of the following problems remains in the proposed sealers for root canal filling. That is, a zinc oxide-eugenol based sealer for root canal filling consisting of a powder material containing zinc oxide as a main component and a liquid material containing eugenol as a main component is the most commonly used in clinical practice. However, the zinc oxide-eugenol based sealer for root canal filling has a strong unpleasant odor which is peculiar to eugenol, poor wettability to the tooth because of hydrophobicity. Furthermore, there is concern about a harmful action to the living body caused by eugenol.

A fatty acid based sealer for root canal filling consisting of a powder material containing zinc oxide as a main component and a liquid material containing, as a main component, an organic unsaturated fatty acid, an organic saturated fatty acid and a multivalent alcohol has been proposed as a sealer for root canal filling which improves a problem in a zinc oxide-eugenol based sealer for root canal filling and reduces an odor and a harmful action to the living body (Japanese Unexamined Patent Application Publication No. S60-181004). However, this sealer also has a characteristic odor, and because this sealer is hydrophobic, this sealer also has poor wettability to the tooth substance.

A calcium phosphate/apatite based sealer for root canal filling consisting of a powder material containing α-TCP, and hydroxyapatite as a main component and a liquid material containing a polycarboxylic acid aqueous solution as a main component (Japanese Unexamined Patent Application Publication No. S62-19508), and a calcium phosphate based sealer for root canal filling consisting of a powder material containing tetra calcium phosphate and secondary calcium phosphate as a main component and a liquid material containing a polycarboxylic acid aqueous solution as a main component (Japanese Unexamined Patent Application Publication No. H2-250811) have been proposed as a sealer for root canal filling having an excellent biocompatibility. Although these sealers are hydrophilic and have good wettability to the tooth substance, these have a low X-ray contrast property, an acid odor due to the polycarboxylic acid, and an irritation to an apical periodontal tissue caused by a strong acidity immediately after kneading.

A dental sealer kit for root canal filling consisting of a resin based sealer for root canal filling containing a monofunctional polymerizable monomer including a polymerizable monomer having an acidic group, a polymerization initiator, an X-ray contrasting filler, and a polymer that swells with the monofunctional polymerizable monomer as a main component and a tooth surface treatment agent suitable for a combination with the resin based sealer for root canal filling, has been proposed as a sealer system for root canal filling having moderate fluidity, a long operation surplus time, and an excellent X-ray contrast property and an excellent sealing property (Japanese Patent Publication No. 3638615). However, this sealer requires tooth surface treatment and therefore the operation is complicated. In addition, there is a concern that a harmful action to the living body due to dissolution of unpolymerized polymerizable monomer and a formation of a gap between the sealer and the tooth substance due to polymerization shrinkage. Furthermore, since the strength of the cured product is high, it is difficult to remove the cured product in re-treatment of a root canal.

A glass ionomer based root sealer for root canal filling in which a powder material containing a fluoroaluminosilicate glass powder and a filler which does not react with polycarboxylic acid, and a polycarboxylic acid aqueous solution are kneaded for use, has been proposed as a sealer for root canal filling having an excellent sealing property, an excellent biocompatibility, and excellent removability of a cured product in re-treatment of a root canal (Japanese Unexamined Patent Application Publication No. 2002-220314). However, because this sealer has a high curing rate, it does not have a sufficient operation surplus time. Further, this sealer has an acid odor due to the polycarboxylic acid, and an irritation to an apical periodontal tissue caused by a strong acidity immediately after kneading.

SUMMARY OF THE INVENTION

Technical Problem

An object of the present disclosure is to provide a sealer composition for root canal filling which has good wettability to the tooth substance, a low unpleasant odor, a low irritation, a low harmful action, an excellent biocompatibility, a sufficient operation surplus time suitable for root canal filling, and excellent dimensional stability after curing, and wherein a cured product of the sealer composition for root canal filling can be easily removed in re-treatment of a root canal.

Solution to Problem

Carboxylate cement in which zinc oxide powder which is an acid reactive inorganic powder and a polycarboxylic acid aqueous solution are kneaded for use, and glass ionomer cement in which fluoroaluminosilicate glass which is an acid reactive inorganic powder and a polycarboxylic acid aqueous solution are kneaded for use, have been used for a long time and widely used in clinical practice as a lining material, a cementing material, a filling material and the like. However, these have an acid odor, and do not have a sufficient operation surplus time because of a high curing rate. In addition, these have an irritation to an apical periodontal tissue because these have low pH immediately after kneading. Further, it is difficult to remove a cured product in re-treatment of a root canal because of the high strength of the cured product. Therefore, these are not suitable for use in root canal filling. In view of the above, the present inventors have found that a composition consisting of a liquid material containing a polymer of an acid group-containing polymerizable monomer in which a portion or the entirety of the acidic group in a molecule forms a salt with an alkaline metal and water, and wherein the pH of the liquid material is in the range from 3.5 to 5.5, instead of a polycarboxylic acid aqueous solution, and a powder material containing an acid reactive inorganic powder has a low acidic odor and a low irritation due to high pH of a kneaded material, and an operation surplus time suitable for root canal filling, and shows moderate mechanical strength wherein a cured product can be easily removed in re-treatment of a root canal. In particular, it has been found that when zinc oxide is contained as an acid reactive inorganic powder in a specific ratio, the removability of a cured product is more excellent while maintaining a sufficient operation surplus time. Further, it has been found that when a glass powder containing an acid-reactive element is contained at a specific ratio in addition to zinc oxide, while maintaining a sufficient operation surplus time and excellent removability of the cured product, the stimulation is reduced because the pH of the kneaded material rapidly transfer to a neutral, leading to completion of the present disclosure.

Specifically, provided is a sealer composition for root canal filling consisting of a liquid material containing a polymer (a) of an acid group-containing polymerizable monomer in which a portion or the entirety of the acidic group in a molecule forms a salt with an alkaline metal and water (b), wherein the pH of the liquid material is in the range from 3.5 to 5.5, and a powder material containing an acid reactive inorganic powder (c). It is preferable that the polymer (a) of an acid group-containing polymerizable monomer in which a portion or the entirety of the acidic group in a molecule forms a salt with an alkaline metal is a polymer of α-β unsaturated carboxylic acid in which a portion or the entirety of the acidic group in a molecule forms a salt with an alkaline metal. It is preferable that the acid reactive inorganic powder (c) contains zinc oxide, or contains zinc oxide and an acid-reactive element-containing glass powder. It is preferable that an operation surplus time at 23° C. is 10 minutes or more.

Advantageous Effects of Invention

The sealer composition for root canal filling of the present disclosure may reduce the burden on patients during treatment due to the reduction of an unpleasant odor, and has an excellent biocompatibility with a low irritation and a low harmful action, so that safety to living body is improved. In addition, since the sealer composition for root canal filling of the present disclosure has a sufficient operation surplus time, it is possible to accurately perform root canal filling. Further, since dimensional change after curing is small, a good prognostic process can be expected. Furthermore, because a cured product may be easily removed when it becomes necessary to re-treatment of a root canal, there is no danger of damaging the tooth substance. Therefore, the sealer composition for root canal filling of the present disclosure can greatly contribute to endodontic therapy.

DETAILED DESCRIPTION OF THE PREFERRED EMBODIMENTS

Hereinafter, each component of a sealer composition for root canal filling of the present disclosure will be described in detail below.

A polymer (a) of an acid group-containing polymerizable monomer in which a portion or the entirety of the acidic group in a molecule forms a salt with an alkaline metal used in the liquid material of the sealer composition for root canal filling of the present disclosure may be any polymer without any limitation as long as a portion or the entirety of the acidic group in a molecule forms a salt with an alkaline metal in the polymer of the acid group-containing polymerizable monomer described below.

As the acidic group-containing polymerizable monomers which may be used for obtaining the polymer of acidic group-containing polymerizable monomer in which a portion or the entirety of the acidic group in a molecule forms a salt with an alkaline metal, any acidic group-containing polymerizable monomers may be used regardless of the type of acidic group. In addition, any acidic group-containing polymerizable monomers may be used regardless of the number or the type of radical polymerizable unsaturated groups (monofunctional groups or multifunctional groups) of the acidic group-containing polymerizable monomer.

Specific examples of the acidic group of the acidic group-containing polymerizable monomer are not limited to, but include a phosphoryl group, a pyrophosphoryl group, a phosphonyl group, a carboxyl group, a sulfonyl group, and a thiophosphoryl group.

Specific examples of the unsaturated group of the acidic group-containing polymerizable monomer are not limited to, but include a (meth) acryloyl group, a styryl group, a vinyl group, and an aryl group. It is preferable that an acidic group-containing polymerizable monomer has a (meth) acryloyl group among these unsaturated groups.

Further, these acidic group-containing polymerizable monomers may contain together other functional group such as an alkyl group, halogen, an amino group, a glycidyl group, and a hydroxy group in a molecule.

Specific examples of an acidic group-containing polymerizable monomers which may be used for obtaining the polymer of acidic group-containing polymerizable monomer in which a portion or the entirety of the acidic group in a molecule forms a salt with an alkaline metal, and has a (meth) acryloyl group as an unsaturated group, are specifically listed below.

Specific examples of an acidic group-containing polymerizable monomer which has a phosphoryl group are not limited to, but include (meth)acryloyloxymethyl dihydrogen phosphate, 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth) acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, bis [2-(meth) acryloyloxyethyl] hydrogensphosphate, bis [3-(meth) acryloyloxypropyl] hydrogen phosphate, bis [4-(meth) acryloyloxybutyl] hydrogen phosphate, bis [6-(meta) acryloyloxyhexyl] hydrogen phosphate, bis [8-(meth) acryloyloxyoctyl] hydrogen phosphate, bis [9-(meth) acryloyloxynonyl] hydrogen phosphate, bis [10-(meth) acryloyloxydecyl] hydrogen phosphate, 1,3-di(meth) acryloyloxypropyl-2-dihydrogenphosphate, 2-(meth) acryloyloxyethylphenyl hydrogen phosphate, and 2-(meth) acryloyloxyethyl 2'-bromoethyl hydrogen phosphate.

Specific examples of an acidic group-containing polymerizable monomer which has a pyrophosphoryl group are not limited to, but include, bis [2-(meth) acryloyloxyethyl] pyrophosphate, bis [3-(meth) acryloyloxypropyl] pyrophosphate, bis [4-(meth) acryloyloxybutyl] pyrophosphate, bis [5-(meth) acryloyloxypentyl] pyrophosphate, bis [6-(meth) acryloyloxyhexyl] pyrophosphate, bis [7-(meth) acryloyloxyheptyl] pyrophosphate, bis [8-(meth) acryloyloxyoctyl] pyrophosphate, bis [9-(meth) acryloyloxynonyl] pyrophosphate, bis [10-(meth) acryloyloxydecyl] pyrophosphate, bis [12-(meth) acryloyloxydodecyl] pyrophosphate, and tris [2-(meth) acryloyloxyethyl] pyrophosphate.

Specific examples of an acidic group-containing polymerizable monomer which has a phosphonyl group are not limited to, but include 5-(meth) acryloyloxypentyl-3-phosphonopropionate, 6-(meth) acryloyloxyhexyl-3-phosphonopropionate, 10-(meth) acryloyloxydecyl-3-phosphonopropionate, 6-(meth) acryloyloxyhexyl-3-phosphonoacetate, and 10-(meth) acryloyloxydecyl-3-phosphonoacetate.

Specific examples of an acidic group-containing polymerizable monomer which has a carboxyl group are not limited to, but include (meth) acrylic acid, 2-chloro acrylic acid, 3-chloro(meth)acrylic acid, 2-cyano acrylic acid, aconitic acid, mesaconic acid, maleic acid, maleic anhydride, itaconic acid, itaconic anhydride, fumaric acid, glutaconic acid, citraconic acid, utraconic acid, 1,4-di(meth) acryloyloxyethylpyromellitic acid, 6-(meth) acryloyloxynaphthalene-1,2,6-tricarboxylic acid, 1-buten-1,2,4-tricarboxylic acid, 3-buten-1,2,3-tricarboxylic acid, N-(meth) acryloyl-p-aminobenzoic acid, N-(meth) acryloyl-5-aminosalicylic acid, 4-(meth) acryloyloxyethyltrimellitic acid and anhydride thereof, 4-(meth) acryloyloxybutyltrimellitic acid and anhydride thereof, 2-(meth) acryloyloxybenzoic acid, 6-(meth) acryloyloxyethyl hydrogen succinate, 6-(meth) acryloyloxyethyl hydrogen maleate, 11-(meth) acryloyloxy-1,1-undecanedicarboxylic acid, p-vinylbenzoic acid, 4-(meth) acryloyloxyethoxycarbonylphthalic acid, 4-(meth) acryloyloxybutyloxycarbonylphthalic acid, 4-(meth) acryloyloxyhexyloxycarbonylphthalic acid, 4-(meth) acryloyloxyoctyloxycarbonylphthalic acid, 4-(meth) acryloyloxydecyloxycarbonylphthalic acid and anhydride thereof, 5-(meth) acryloylaminopentylcarboxylic acid, 6-(meth) acryloyloxy-1,1-hexanedicarboxylic acid, 8-(meth) acryloyloxy-1,1-octanedicarboxylic acid, 10-(meth) acryloyloxy-1,1-decanedicarboxylic acid, and 11-(meth) acryloyloxy-1,1-undecanedicarboxylic acid.

Specific examples of an acidic group-containing polymerizable monomer which has a sulfonate group are not limited to, but include 2-(meth) acrylamido-2-methylpropanesulfonic acid, styrenesulfonic acid, 2-sulfoethyl (meth) acrylate, 4-(meth) acryloyloxy benzenesulfonic acid, and 3-(meth) acryloyloxy propanesulfonic acid.

Specific examples of an acidic group-containing polymerizable monomer which has a thiophosphoryl group are not limited to, but include, 2-(meth) acryloyloxyethyl dihydrogendithiophosphate, 3-(meth) acryloyloxypropyl dihydrogendithiophosphate, 4-(meth) acryloyloxybutyl dihydrogendithiophosphate, 5-(meth) acryloyloxypentyl dihydrogendithiophosphate, 6-(meth) acryloyloxyhexyl dihydrogendithiophosphate, 7-(meth) acryloyloxyheptyl dihydrogendithiophosphate, 8-(meth) acryloyloxyoctyl dihydrogendithiophosphate, 9-(meth) acryloyloxynonyl dihydrogendithiophosphate, 10-(meth) acryloyloxydecyl dihydrogendithiophosphate.

These acidic group-containing polymerizable monomers can be used not only singly but also in combinations of a plurality thereof for synthesize a polymer of the acidic group-containing polymerizable monomer. Furthermore, the polymer of the acidic group-containing polymerizable monomer may be obtained by copolymerizing a polymerizable monomer containing one or more acidic group in a molecule and a polymerizable monomer containing no acidic group, without any problem.

It is preferable to use an α-β unsaturated carboxylic acid based acidic group-containing polymerizable monomers among these acidic group-containing polymerizable monomers having an acidic group or by copolymerizing two or more of them. The α-β unsaturated carboxylic acid based acidic group-containing polymerizable monomer is not particularly limited and may be used regardless of the number of carboxylic groups in the molecule or the existence of a carboxylic anhydride group or other substituents.

Specific examples of an α-β unsaturated carboxylic acid based acidic group-containing polymerizable monomer are not limited to, but include (meth) acrylic acid, 2-chloro acrylic acid, 3-chloro (meth) acrylic acid, 2-cyano acrylic acid, aconitic acid, mesaconic acid, maleic acid, maleic anhydride, itaconic acid, itaconic anhydride, fumaric acid, glutaconic acid, citraconic acid, utraconic acid, 1-buten-1,2,4-tricarboxylic acid, and 3-buten-1,2,3-tricarboxylic acid. It is preferable to use a polymer of an acid group-containing polymerizable monomer synthesized from only acrylic acid as a starting material or a polymer of an acid group-containing polymerizable monomer synthesized from two or more kinds of starting materials such as acrylic acid and maleic acid, acrylic acid and maleic anhydride, acrylic acid and itaconic acid, acrylic acid and 3-butane-1,2,3-tricarboxylic acid.

The method of polymerizing various polymerizable monomers is not particularly limited, and a polymer polymerized by any methods such as solution polymerization, suspension polymerization, emulsion polymerization or the like, may be used without any limitation. In addition, a polymerization initiator and a chain transfer agent used at the time of synthesis of a polymer may be appropriately selected in order to obtain a desired polymer.

A weight average molecular weight of the polymer of an acid group-containing polymerizable monomer is not limited particular, but preferably is in a rage of 10000 to 200000, more preferable in a rage of 10000 to 100000.

When a weight average molecular weight of the polymer of an acid group-containing polymerizable monomer decreases below 10000, the mechanical strength of a cured product may tend to decrease too much to cause problem in durability of the cured product. On the other hand, when a weight average molecular weight of the acid group-containing polymerizable monomer increases above 200000, viscosity of the kneaded material of the liquid material and the powder material which constitute a sealer composition for root canal filling may become higher to cause problems in a filling property to a root canal.

Then, the obtained polymer of an acid group-containing polymerizable monomer is then reacted with an alkali metal hydroxide such as sodium hydroxide, potassium hydroxide and lithium hydroxide, an alkali metal carbonate such as sodium carbonate, potassium carbonate and lithium carbonate, and a bicarbonate of an alkali metal such as sodium hydrogen carbonate, potassium hydrogen carbonate, lithium hydrogen carbonate or the like, to make a portion or the entirety of the acidic group an alkali metal salt. Thereby, the polymer (a) of an acid group-containing polymerizable monomer in which a portion or the entirety of the acidic group in a molecule forms a salt with an alkaline metal is obtained. There is no problem even if alkali metals that form salt with acidic group may be used alone or in combination of two or more thereof for forming salt with acidic group. Furthermore, the polymer (a) of an acid group-containing polymerizable monomer in which a portion or the entirety of the acidic group in a molecule forms a salt with an alkaline metal may partially form salt with a divalent metal such as magnesium, calcium, strontium, barium, and zinc, a trivalent metal such as aluminum, lanthanum, chromium, ytterbium, or a tetravalent metal such as titanium, zirconium or the like without any problem. The metal forming the salt is not limited to these, and there is no problem even if the metal may be used alone or in combination of two or more thereof for forming salt with acidic group.

A molecular weight of the polymer of an acid group-containing polymerizable monomer in which a portion or the entirety of the acidic group in a molecule forms a salt with an alkaline metal, is not limited particular, but preferably is in the same range as that of the polymer of an acid group-containing polymerizable monomer before reacting with the above described an alkali metal hydroxide, an alkali metal carbonate, an alkali metal hydrogencarbonate or the like.

Furthermore, the polymer of an acid group-containing polymerizable monomer in which a portion or the entirety of the acidic group in a molecule forms a salt with an alkaline metal may be synthesized by reacting an acid group-containing polymerizable monomer having at least one acid group in molecule with the above described an alkali metal hydroxide, an alkali metal carbonate, an alkali metal hydrogencarbonate or the like to make a portion or the entirety of the acidic group a salt with an alkaline metal, and then by polymerizing the reaction product alone, copolymerizing two or more kinds of the reaction products, or copolymerizing the reaction product with a polymerizable monomer not having an acidic group.

The polymer of an acid group-containing polymerizable monomer in which a portion or the entirety of the acidic group in a molecule forms a salt with an alkaline metal may be supplied in a state of coexisting with water which is used as a solvent in the synthesis. Further, the polymer of an acid group-containing polymerizable monomer in which a portion or the entirety of the acidic group in a molecule forms a salt with an alkaline metal may be supplied in powder form to the powder material of the sealer composition for root canal filling of the present disclosure as a component.

Any water can be used as the water (b) used in the liquid material of the sealer composition for root canal filling of the present disclosure, without any limitation as far as it does not contain impurities adversely affecting on the curability and mechanical strength of the sealer composition for root canal filling. Specifically, it is preferably to use distilled water or ion-exchanged water.

It is essential of the present disclosure that the pH of the liquid material of the sealer composition for root canal filling containing of the polymer of an acid group-containing polymerizable monomer in which a portion or the entirety of the acidic group in a molecule forms a salt with an alkaline metal and water of the present disclosure is in the range from 3.5 to 5.5. More preferable range is from 3.5 to 5.0. When the pH is lower than 3.5, an acid smell becomes strong and the sealer composition for root canal filling has an irritation to an apical periodontal tissue. In addition, because the curing rate becomes faster, the sealer composition for root canal filling did not have a sufficient operation surplus time suitable for root canal filling. Further, the mechanical strength of the cured product became too high and it becomes difficult to remove in re-treatment of a root canal. On the other hand, when the pH is higher than 5.5, the mechanical strength of the cured product tends to decrease too much to cause problems in durability of the cured product.

As the acid reactive inorganic powder (c) used in the powder material of the sealer composition for root canal filling of the present disclosure, any acid reactive inorganic powder as long as the acid reactive inorganic powder contains element which may form chelate-bond with an acid group of the polymer of an acid group-containing polymerizable monomer in which a portion or the entirety of the acidic group in a molecule forms a salt with an alkaline metal, or with an alkaline metal salt of this acid group, can be used without any limitation. That is, it is necessary to contain a metal element belonging to groups I to XVI of the periodic table. Specific examples include lithium, sodium, potassium, magnesium, calcium, strontium, barium, lanthanum, aluminum, titanium, chromium, iron, cobalt, nickel, copper, zinc, zirconium, ytterbium, and the like, but it is not limited thereto. Among these, it is more preferable to use an acid reactive inorganic powder containing a divalent metal element such as magnesium, calcium, strontium, barium, nickel, copper, zinc and the like.

The acid reactive inorganic powder may contain one or two or more kinds of these metal elements, and a content thereof is not particularly limited. Further, element to be contained in the acid reactive inorganic powder other than these metal elements is not particularly limited, and the acid reactive inorganic powder in the present disclosure may contain various elements.

That is, as the acid reactive inorganic powder contained in the powder material of the present disclosure, oxide, hydroxide, sulfate, nitrate, phosphate, carbonate, silicate, fluoride, nitride, mineral, and glass may be used without any limitation as far as it contains the above described metal element. Specific examples of the acid reactive inorganic powder include magnesium oxide, zinc oxide, titanium oxide, aluminum oxide, zirconium oxide, aluminum silicate, an acid-reactive element-containing glass (including a glass by melting method, a glass produced by a vapor phase reaction, synthetic glass by sol-gel method and the like), strontium fluoride, calcium carbonate, mica, aluminum sulfate, calcium sulfate, barium sulfate, calcium phosphate, calcium hydroxide, calcium aluminate, strontium hydroxide, zinc fluoride, ytterbium fluoride, zeolite, hydroxyapatite, and aluminum nitride, but is not limited thereto.

These acid reactive inorganic powders may be used alone or in combination of two or more thereof. These acid reactive inorganic powders exhibiting any property of insolubility, hard solubility or easy solubility in water may be used without any problem. Further, a shape of the acid reactive inorganic powder is not particularly limited, but arbitral particle shapes such as spherical, needle-like, plate-like, ground-like, and scaly-shapes and aggregate thereof may be used without any limitation.

Furthermore, as far as a reaction of the powder material and the liquid material is not adversely affected, for the purpose of imparting excellent various properties to the sealer composition for root canal filling of the present disclosure or for other purpose, the acid reactive inorganic powder may be subjected to secondary processing to adjust the reactivity or to impart multifunctionality. Specific examples of the secondary processing include heat treatment of heating the acid reactive inorganic powder at an elevated temperature in an electric furnace or the like, complex oxidation process of complexing two or more kinds of acid reactive inorganic powders or two or more kinds of acid reactive inorganic powder and other inorganic powder by mixing, reaction, crushing and dispersing using various methods, grinding process of grinding the acid reactive inorganic powder using a grinder, and surface modification process of modifying a surface of the acid reactive inorganic powder by surface treating agent or other methods.

Specific examples of a surface treating agent include a surfactant, an organic acid, an inorganic acid, a silane coupling agent, a titanate coupling agent, and polysiloxane.

Specific examples of a method of surface modification process include aggregating treatment in which the acid reactive inorganic powders are aggregated in a liquid phase or a vapor phase, and heat-treated thereafter, microcapsulation in which a surface of the acid reactive inorganic powder is enclosed with an organic substance, and grafting in which a surface of the acid reactive inorganic powder is functionalized with an organic substance.

The secondary processing such as heat treatment, complex oxidation process, grinding process and surface modification process may be used alone or in combination of two or more thereof.

On the other hand, high X-ray contrast property is required in the sealer for root canal filling in order to accurately carry out the conformation and prognosis follow-up observation of filling state to the root canal. Therefore, it is preferable that the acid reactive inorganic powder contains zinc, zirconium, barium, strontium, lanthanum, titanium, yttrium, ytterbium, tantalum, tin, tellurium, tungsten and bismuth or the like as the element that blocks X-ray. Specific examples include zinc oxide, zirconium oxide, strontium oxide, yttrium oxide, titanium oxide, barium oxide, lanthanum oxide, ytterbium oxide, bismuth oxide, barium sulfate, ytterbium fluoride, lanthanum fluoride, yttrium fluoride, titanium fluoride, silica-zirconia, silica-titania, as well as aluminosilicate glass, borosilicate glass, aluminoborate glass, boro aluminosilicate glass, phosphate glass, borate glass, silica glass wherein these glasses contain the above described element that blocks X-ray, but not limited.

An average particle diameter of the acid reactive inorganic powder is preferably in the range from 0.05 to 30.0 μm, more preferably in the range from 0.05 to 20.0 μm, further preferably in the range from 0.05 to 10.0 μm. When an average particle diameter of the acid reactive inorganic powder is less than 0.05 μm, since the surface area is increased, adaptability to the liquid material may become bad to decrease kneadability, and the viscosity of the kneaded material increases to cause problems in a filling property to a root canal. Furthermore, because reactivity becomes higher, the sealer composition for root canal filling may not have a sufficient operation surplus time. When an average particle diameter of the acid reactive inorganic powder is more than 30.0 μm, the mechanical strength becomes higher, therefore it may be difficult to remove the cured product in re-treatment of a root canal. Among the above acid-reactive inorganic powder, it is preferable to use zinc oxide because of that excellent removability of the cured product while having a sufficient operation surplus time. It is preferable that the content of zinc oxide is 50 part by weight or more for the whole amount of the acid reactive inorganic powder. In the case that zinc oxide is contained in the form of a composite oxide, the content of zinc oxide calculated by excluding the content of other metal oxides in the composite oxide may be 50 part by weight or more for the whole amount of the acid reactive inorganic powder. When the content of zinc oxide is less than 50 part by weight for the whole amount of the acid reactive inorganic powder, the mechanical strength may become higher, therefore the removability of the cured product decreases.

Further, it is preferable that an acid-reactive element-containing glass powder is contained as an acid reactive inorganic powder in addition to the zinc oxide because the pH of kneaded material rapidly transfer to a neutral to more reduce an irritation. It is preferable that the content of the acid-reactive element-containing glass powder is 5 to 40 part by weight for the whole amount of the acid reactive inorganic powder, more preferably 10 to 30 part by weight for the whole amount of the acid reactive inorganic powder. When the content of the acid-reactive element-containing glass powder is less than 5 part by weight for the whole amount of the acid reactive inorganic powder, the rate at which the pH of the kneaded material transfer to a neutral may not become fast enough. Further, when the content of the acid-reactive element-containing glass powder exceeds 40 part by weight, an operation surplus time may become shortened.

A preparing process of the acid-reactive element-containing glass powder is not particularly limited, but an acid-reactive element-containing glass powder prepared by any process such as a melting process, a vapor phase process and a sol-gel process may be used without any problem. Among them, the acid-reactive element-containing glass powder prepared by a melting process or a sol-gel process which can easily control a kind of element contained in the acid-reactive element-containing glass powder and the content thereof is preferably used.

As the acid-reactive element-containing glass powder, those which are generally sold may be used without processing such as grinding, but it is preferable to use those after grinding into a desired average particle diameter in order to control reactivity of the sealer composition for root canal filling of the present disclosure. A grinding method is not particularly limited, but an acid-reactive element-containing glass powder obtained by grinding which use any of wet or dry grinding methods may be used. Specifically, a desirable average particle diameter is obtained by a high speed rotating mill such as a hammer mill and a turbo-mill, a container driving medium mill such as a ball mill and a vibration mill, a medium stirring mill such as a sand grinder and attritor, and a jet mill and the like.

In a preferable aspect, in order to control reactivity of the sealer composition for root canal filling of the present disclosure, the acid-reactive element-containing glass powder is subjected to polysiloxane treatment wherein the surface is coated with polysiloxane. That is, an operation surplus time and a curing time after kneading the liquid material and the powder material which constitute a sealer composition for root canal filling of the present disclosure may be arbitrarily controlled by polysiloxane treatment.

Specific examples of a silane compound which can be used in this polysiloxane treatment are not limited to, but include tetramethoxysilane, tetraethoxysilane, tetrapropoxysilane, tetraallyloxysilane, tetrabutoxysilane, tetrakis(2-ethylhexyloxy)silane, trimethoxychlorosilane, triethoxychlorosilane, triisopropoxychlorosilane, trimethoxyhydroxysilane, diethoxydichlorosilane, tetraphenoxysilane, tetrachlorosilane, silicon hydroxide (silicon oxide hydrate) and a low condensate of those silane compounds.

Among these silane compounds, tetramethoxysilane, tetraethoxysilane and a low condensate of those silane compounds are preferable, and tetramethoxysilane and a low condensate of tetraethoxysilane are more preferable. These silane compounds may be used singly or in combination.

In the sealer composition for root canal filling of the present disclosure, a cured product is prepared by kneading the liquid material containing the polymer (a) of an acid group-containing polymerizable monomer in which a portion or the entirety of the acidic group in a molecule forms a salt with an alkaline metal and the water (b), and the powder material containing the acid reactive inorganic powder (c).

It is preferable that the content of the polymer (a) of the acid group-containing polymerizable monomer in which a portion or the entirety of the acidic group in a molecule forms a salt with an alkaline metal is in the range from 3 to 20 part by weight in the cured product prepared by kneading the liquid material and the powder material. When the content of the polymer (a) of the acid group-containing polymerizable monomer in which a portion or the entirety of the acidic group in a molecule forms a salt with an alkaline metal is less than 3 part by weight, the mechanical strength of the cured product may tend to decrease too much to cause problems in durability of the cured product. When the content of the polymer (a) of the acid group-containing polymerizable monomer in which a portion or the entirety of the acidic group in a molecule forms a salt with an alkaline metal exceeds 20 part by weight, viscosity of a kneaded material of the liquid material and the powder material may become higher to cause problems in a filling property to a root canal, and the sealer composition for root canal filling may not have a sufficient operation surplus time.

It is preferable that the content of the water (b) in the cured product prepared by kneading the liquid material and the powder material is in the range from 10 to 60 part by weight. When the content of the water (b) is less than 10 part by weight, viscosity of the kneaded material of the liquid material and the powder material may become higher to cause problems in a filling property to a root canal. In addition, because the curing rate becomes faster, the sealer composition for root canal filling may not have a sufficient operation surplus time suitable for root canal filling. Further, the strength of the cured product may become too high and it may become difficult to remove in re-treatment of a root canal. When the content of the water (b) exceeds 60 part by weight, the mechanical strength of the cured product may tend to decrease too much to cause problems in durability of the cured product.

It is preferable that the content of the acid reactive inorganic powder (c) in the cured product prepared by kneading the liquid material and the powder material is in the range from 30 to 85 part by weight. When the content of the acid reactive inorganic powder (c) is less than 30 part by weight, the mechanical strength of the cured product may tend to decrease too much to cause problems in durability of the cured product. When the content of the acid reactive inorganic powder (c) exceeds 85 part by weight, viscosity of the kneaded material of the liquid material and the powder material may become higher to cause problems in a filling property to a root canal.

On the other hand, a sealer for root canal filling is generally filled in a root canal with a plurality of gutta-percha point in clinical, while the kneaded material thereof maintains paste form having fluidity. Specific filling methods is as follows. First, a sealer for root canal filling is kneaded to prepare a kneaded material, and appropriate amount of the kneaded material is filled in a root canal. Then gutta-percha points applied with the kneaded material are prepared, and the gutta-percha points are inserted into the root canal sequentially one by one. Finally, the root canal is filled with a plurality of gutta-percha points and the kneaded material.

For accurately performing root canal filling, it is preferable that the operation surplus time at 23° C. of the sealer composition for root canal filling of the present disclosure is 10 minutes or more. In the present disclosure, "operation surplus time" refers to a period of time from the start of kneading the liquid material and the powder material to the time wherein the kneaded material loses the fluidity. In the present disclosure, "the kneaded material loses the fluidity" refers to a state that the kneaded material cannot be easily applied on a gutta-percha point which is filled in the root canal along with the sealer for root canal filling in clinical, by changing the kneaded material from paste form having fluidity to putty form. When the operation surplus time is shorter than 10 minutes, viscosity of the kneaded material increase during treatment, therefore there is a risk that the kneaded material cannot be tightly filled in the root canal. Further, in the case of treating teeth having a plurality of root canals, viscosity of the kneaded material may increase before completion of filling operation of all the root canals. Therefore, because it is necessary to prepare a kneaded material again, and operation may be complicated.

The powder material of the sealer composition for root canal filling of the present disclosure may contain a second powder which is other than the acid reactive inorganic powder. As the second powder, a powder which does not contain element which forms chelate-bond with the acid group of the polymer of an acid group-containing polymerizable monomer in which a portion or the entirety of the acidic group in a molecule forms a salt with an alkaline metal, or alkaline metal salt of this acid group, may be used without any limitation. Examples of the second powder include known dental fillers such as an inorganic filler, an organic filler and an organic-inorganic complex filler, and these can be used alone or in a combination of a few of them without any limitation. In addition, a shape of these second fillers is not particularly limited, but arbitral particle shapes such as spherical, needle-like, plate-like, ground-like, and scaly-shapes and aggregate thereof may be used.

Specific examples of the inorganic filler include quartz, amorphous silica, ultrafine silica, various glasses which does not contain element which may form chelate-bond with an acid group or alkaline metal salt of an acid group (including a glass by melting method, a glass produced by a vapor phase reaction, synthetic glass by sol-gel method and the like), silicon nitride, silicon carbide, boron carbide and the like, but is not limited thereto.

An average particle diameter of these inorganic fillers is not particularly limited, but is preferably in the range from 0.001 to 30 μm.

As the organic filler, any organic filler obtained by polymerizing a monomer having a polymerizable group may be used without any limitation, and the type of the organic filler is not specifically limited.

Specific examples of the organic filler include an organic filler obtained by polymerizing a single or (co)polymerizing a plurality of polymerizable monomer such as unsaturated aromatics such as styrene, α-methylstyrene, halogenated styrene, and divinylbenzene; unsatuated esters such as vinyl acetate and vinyl propionate; unsatuated nitriles such as acrylonitrile; butadiene and isoprene. Particularly preferable are organic fillers obtained by polymerizing various polymerizable monomers which have been already known and used in the dental field.

The preparation method of the organic filler is not particularly limited, and any method such as emulsion polymerization, suspension polymerization or dispersion polymerization of the monomer having a polymerizable group, or a method for pulverizing a polymer bulk previously produced can also be conducted.

An average particle diameter of the organic filler is preferably in the range from 1 to 100 μm, more preferably 3 to 50 μm, further preferably 5 to 30 μm.

Further, an organic-inorganic complex filler having a structure in which inorganic fillers are enclosed in an organic polymer may be used. The inorganic filler to be enclosed in an organic polymer is not particularly limited, and known organic fillers can be used. For example, the aforementioned inorganic fillers which can be used as a second powder can be used.

Further, in the organic-inorganic complex filler, since an inorganic filler is enclosed in an organic polymer, the aforementioned acid reactive fillers may be used as the inorganic filler to be contained in the organic-inorganic complex filler as far as an acid group of the polymer of an acid group-containing polymerizable monomer in which a portion or the entirety of the acidic group in a molecule forms a salt with an alkaline metal, or alkaline metal salt of this acid group do not forms chelate-bond.

A process for preparing an organic-inorganic complex filler is not particularly limited, but any process can be adopted. Examples include a process of microcapsulating or grafting a surface of an inorganic filler with an organic substance, a process of introducing a polymerizable functional group or a polymerizable initiating group into a surface of an inorganic filler, and radical-polymerizing an organic monomer on the surface, and a process of grinding an organic polymer bulk containing a previously produced inorganic filler.

An average particle diameter of these organic-inorganic complex fillers is preferably in the range from 1 to 100 μm, more preferably in the range from 3 to 50 μm, further preferably in the range from 5 to 30 μm.

These second powders may be used alone or in combination of two or more thereof.

A surface of each of an inorganic filler, an organic filler, and an organic-inorganic complex filler used as a second powder may be subjected to surface treatment by use of a surface treating agent or other surface treating method to improve wettability to water and to impart multifunctionality.

Examples of the surface treating agent which can be used in surface treatment are not limited to, but include a surfactant, an organic acid, an inorganic acid, a silane coupling agent, a titanate coupling agent, and polysiloxane. A surface treating method which can be used in surface treatment is not particularly limited, but the known methods can be used.

These surface treating agents and surface treating methods can be used alone, or in a combination thereof.

A content of the second powder which is contained in the powder material of the sealer composition for root canal filling of the presents disclosure may be arbitrarily set depending on the requirement for the material properties required in the sealer composition for root canal filling of the present disclosure, and is preferably in the range from 1.0 to 20.0 part by weight in the cured product obtained by kneading the liquid material and powder material.

A polybasic carboxylic acid, a phosphoric acid, a pyrophosphoric acid or a tripolyphosphoric acid may be contained in the liquid material and/or the powder material of the sealer composition for root canal filling of the present disclosure, for the purpose of adjusting the operation surplus time and curing time. Specific examples of the polybasic carboxylic acid used in the sealer composition for root canal filling of the present disclosure include tartaric acid, citric acid, maleic acid, fumaric acid, malic acid, aconitic acid, tricarballylic acid, itaconic acid, 1-butene-1,2,4-tricarboxylic acid, and 3-butene-1,2,3-tricarboxylic acid, and the like. The aforementioned polybasic carboxylic acid are not limited to these, but can be used without any limitation. A polybasic carboxylic acid, a phosphoric acid, a pyrophosphoric acid and/or a tripolyphosphoric acid may be used alone or in combination of two or more thereof. A content of a polybasic carboxylic acid, a phosphoric acid, a pyrophosphoric acid and/or a tripolyphosphoric acid is preferably in the range from 0.1 to 15.0 part by weight in the cured product obtained by kneading the liquid material and powder material.

Further, a surfactant can be contained in the liquid material of the sealer composition for root canal filling of the present disclosure to such an extent that various properties are not influenced, for the purpose of improving kneadability of the liquid material and powder material.

The surfactant which can be used in the liquid material of the sealer composition for root canal of the present disclosure may be any of an ionic surfactant and a nonionic surfactant.

Examples of the anionic surfactant in the ionic surfactant include aliphatic carboxylic acid metal salts such as sodium stearate, sulfated aliphatic carboxylic acid metal salts such as sodium dioctyl sulfosuccinate, and metal salts of higher alcohol sulfate ester such as sodium stearyl sulfate. In addition, examples of the cationic surfactant include an aduct of higher alkylamine and ethylene oxide, amines made from lower amine, and alkyltrimethylammonium salts such as lauryltrimethylammoniun chloride. Further, examples of the amphoteric surfactant include metal salts of higher alkylaminopropionic acid such as sodium stearylaminopropionate, and betaines such as lauryldimethylbetaine.

Examples of the nonionic surfactant include polyethylene glycol type and polypropylene glycol type in which ethylene oxide or propylene oxide is added to higher alcohols, alkyl phenols, fatty acids, higher fatty amines, or aliphatic amides, and polyhydric alcohol type in which polyhydric alcohols, diethanolamines, or saccharides is ester bonded to a fatty acid.

The aforementioned surfactants are not limited to these, but can be used without any limitation. These surfactants can be used alone, or in a combination of a few kinds.

A content of the surfactant contained in the liquid material of the sealer composition for root canal filling of the present disclosure is preferably in the range from 0.001 to 5.0 part by weight in the cured product obtained by kneading the liquid material and powder material.

Furthermore, the sealer composition for root canal filling of the present disclosure may optionally contain other conventionally known additives such as preservatives, antimicrobial materials, and coloring pigments.

EXAMPLES

Hereinafter, Examples and Comparative Examples of the present disclosure are specifically described. However, the present disclosure is not intended to be limited to these Examples. Test methods for evaluating performances of the sealer composition for root canal filling prepared in each of Examples and Comparative Examples are as follows.

[Odor]

Object: To evaluate an odor of the kneading material of the sealer composition for root canal filling.

Method: Each of the sealer composition for root canal filling of the examples and comparative examples was prepared by kneading each composition at the ratio shown in Table 3. Immediately after kneading, an odor of the obtained kneaded material was confirmed. Odors were evaluated in follows three scales.
A: No odor
B: Slight odor
C: Strong odor

[Kneaded Material pH]

Object: To evaluate the pH of the kneaded material of the sealer composition for root canal filling.

Method: Each of the sealer composition for root canal filling of the examples and comparative examples was prepared by kneading each composition at the ratio shown in Table 3 under the condition of 23° C. and 50% humidity. Immediately after kneading, 2 mL of distilled water was added dropwise on the kneaded material. Immediately after dropwise addition, the supernatant of the dropped distilled water was collected by using a syringe. The collected supernatant was used for measuring the pH by using a desk top type water quality analyzer LAQUA (HORIBA Ltd.).

[Operation Surplus Time]

Object: To evaluate the operation surplus time of the sealer composition for root canal filling.

Method: Each of the sealer composition for root canal filling of the examples and comparative examples was prepared by kneading each composition at the ration shown in Table 3 under the condition of 23° C. and 50% humidity. After kneading, the kneaded material was applied on the gutta-percha point (0.06 taper, #40), and application property was confirmed. This operation was repeated until the kneaded material loses the fluidity. Operation surplus time was set to time from the start of kneading and to the time wherein the kneaded material loses the fluidity, and the kneaded material could not be easily applied on the gutta-percha point.

[Curing Time]

Object: To evaluate curing time of the sealer composition for root canal filling.

Method: Curing time was measured by the following procedure according to ISO 6786: 2012. Each of the sealer composition for root canal filling of the examples and comparative examples was prepared by kneading each composition at the ratio shown in Table 3 under the condition of 23° C. and 50% humidity. After kneading, the kneaded material was filled in a stainless steel mold (10φ×2 mm: cylindrical shape) placed on a glass plate. After 120±10 seconds from the end of kneading, the stainless steel mold filled with the kneaded material was placed on a metal block (minimum size: 8 mm×20 mm×10 mm) in a 37° C. and 100% thermohygrostat. Vicat needle (mass: 100.0±0.5 g, end diameter: 2.0±0.1 mm) was vertically taken down on the horizontal plane of the kneaded material and vestige of the vicat needle was visually observed. This operation was repeated until vestige of vicat needle did not remain. Curing time was set to time from the end of kneading to the time wherein vestige of vicat needle did not remain.

[Compressive Strength]

Object: To evaluate the compressive strength of the sealer composition for root canal filling.

Method: Each of the sealer composition for root canal filling of the examples and comparative examples was prepared by kneading each composition at the ratio shown in Table 3. After kneading, the kneaded material was filled in a stainless steel mold (4φ×6 mm: cylindrical shape) and left in a 37° C. and 100% thermohygrostat for 3 days. The specimen was taken out from the mold after 3 days and an Instron universal tester (Instron 5567A manufactured by Instron) was used to measure the compressive strength at a crosshead speed of 1 mm/min.

[Removability]

Object: To evaluate the removability of the sealer composition for root canal filling.

Method: Each of the sealer composition for root canal filling of the examples and comparative examples was prepared by kneading each composition at the ratio shown in Table 3. After kneading, the kneaded material was applied on the gutta-percha point and the gutta-percha point was filled by method of lateral condensation of filling, in a root canal of the maxillary first premolar which was extracted from human and which was formed with the root canal. After filling, the kneaded material was left in a 37° C. and 100% thermohygrostat for 7 days. The gutta-percha point and the cured product of the sealer composition for root canal filling in the root canal were removed by using hand file after 7 days. Odors were evaluated in follows four scales.
AA: Easily removable
A: Removable
B: A little difficult to remove
C: Difficult to remove Components used in Examples and Comparative Examples of the present disclosure and abbreviations thereof are shown below.

Polymer (a) of an Acid Group-Containing Polymerizable Monomer in which a Portion or the Entirety of the Acidic Group in a Molecule Forms a Salt with an Alkaline Metal In preparing the liquid material, the polymer (a) of an acid group-containing polymerizable monomer in which a portion or the entirety of the acidic group in a molecule forms a salt with an alkaline metal was compounded in the form of an aqueous solution as follows (PCA1 aqueous solution to PCA7 aqueous solution).

PCA1 aqueous solution: Acrylic acid homopolymer sodium salt solution (Weight-average molecular weight: 50000, Solid content concentration: 20 part by weight, pH: 4.2)

PCA2 aqueous solution: Acrylic acid-tricarboxylic acid copolymer sodium salt solution (Weight-average molecular weight: 70000, Solid content concentration: 40 part by weight, pH: 5.5)

PCA3 aqueous solution: Acrylic acid homopolymer sodium salt solution (Weight-average molecular weight: 50000, Solid content concentration: 60 part by weight, pH: 4.5)

PCA4 aqueous solution: Acrylic acid-tricarboxylic acid copolymer sodium salt solution (Weight-average molecular weight: 70000, Solid content concentration: 12 part by weight, pH: 5.3)

PCA5 aqueous solution: Acrylic acid homopolymer sodium salt solution (Weight-average molecular weight: 50000, Solid content concentration: 40 part by weight, pH: 3.0)

PCA6 aqueous solution: Acrylic acid-tricarboxylic acid copolymer sodium salt solution (Weight-average molecular weight: 70000, Solid content concentration: 20 part by weight, pH: 6.2)

PCA7 aqueous solution: Acrylic acid-tricarboxylic acid copolymer sodium salt solution (Weight-average molecular weight: 70000, Solid content concentration: 5 part by weightpart by weight, pH: 5.5)

*Solid content concentration: Content of the polymer of an acid group-containing polymerizable monomer in which a portion or the entirety of the acidic group in a molecule forms a salt with an alkaline metal Acid Reactive Inorganic Powder (c)

G1: Acid reactive inorganic powder 1 (zinc oxide-magnesium oxide-bismuth subnitrate complex oxide, 50% average particle diameter: 3.7 μm)

G2: Acid reactive inorganic powder 2 (fluoro-aluminosilicate glass, 50% average particle diameter: 4.5 μm)

G3: Acid reactive inorganic powder 3 (strontium fluoride, 50% average particle diameter: 15.7 μm)

Other Components

PAA: Acrylic acid homopolymer powder (Weight-average molecular weight: 50000, pH in aqueous solution of solid content concentration of 20 part by weight: <1.0)

*Solid content concentration: Content of acrylic acid homopolymer powder

Silica powder (50% average particle diameter: 3.2 μm)

Tartaric acid

Phosphoric acid

[G1: Preparation of Acid Reactive Inorganic Powder 1]

Various raw materials: zinc oxide, magnesium oxide, and bismuth subnitrate (the composition of the acid reactive inorganic powder: zinc oxide: 87.5 part by weight, magnesium oxide: 10.0 part by weight, bismuth subnitrate: 2.5 part by weight) were mixed and the mixed material was fired at 1240° C. using an electric furnace. The resulting fired material was pulverized to obtain Acid reactive inorganic powder 1. The Acid reactive inorganic powder 1 was measured for 50% average particle diameter by a laser diffraction type particle size measuring apparatus (Microtrac SPA: NIKKISO Co., Ltd.). The result was 3.7 μm.

[G2: Preparation of Acid Reactive Inorganic Powder 2]

Various raw materials: silicon dioxide, aluminum oxide, sodium fluoride, and strontium carbonate (glass composition: $SiO_2$: 23.8 part by weight, $AlO_3$: 16.2 part by weight, SrO: 35.6 part by weight, $Na_2O$: 2.3 part by weight, and F: 11.6 part by weight) were mixed and the mixed material was molten at 1400° C. in a melting furnace. The melt was taken out from the melting furnace, and cooled in water to prepare a glass. The resulting glass was pulverized to obtain Acid reactive inorganic powder 2. The Acid reactive inorganic powder 2 was measured for 50% average particle diameter by a laser diffraction type particle size measuring apparatus (Microtrac SPA: NIKKISO Co., Ltd.). The result was 4.5 μm.

[Preparing Powder Material and Liquid Material]

Liquid materials L1 to L10 were prepared by mixing each component according to each ratio shown in Table 1. Further, powder materials P1 to P14 were prepared by mixing each component according to each ratio shown in Table 2. The sealer compositions for root canal filling (Examples 1 to 24 and Comparative Examples 1 to 8) were prepared by kneading the liquid material and the powder material according to the combination and a powder/liquid ratio shown in Tables 3 and 4 and evaluated for odor, kneaded material pH, operation surplus time, curing time, compressive strength, and removability according to the above described method. Furthermore, four products of commercially available sealer for root canal filling (Comparative Examples 9 to 12) were also evaluated in the same manner. The results are shown in Table 5.

TABLE 1

| | Composition of Liquid material | | | | | | |
|---|---|---|---|---|---|---|---|
| | Aqueous solution of (a) polymer* (wt. %) | | | | | | |
| | Detail | | (b) | Tartaric | Phosphoric | | |
| | (a) polymer | (b) Water | Water | acid | acid | PAA | |
| | Type (wt. %) | (wt. %) | (wt. %) | (wt. %) | (wt. %) | (wt. %) | pH |
| L1 | 100 PCA1 20 | 80 | | | | | 4.2 |
| L2 | 100 PCA2 40 | 60 | | | | | 5.5 |
| L3 | 100 PCA3 60 | 40 | | | | | 4.5 |
| L4 | 100 PCA4 12 | 88 | | | | | 5.3 |
| L5 | 100 PCA5 40 | 60 | | | | | 3.0 |
| L6 | 100 PCA6 20 | 80 | | | | | 6.2 |
| L7 | 95 PCA2 38 | 57 | | 5 | | | 4.2 |
| L8 | 95 PCA2 38 | 57 | | | 5 | | 3.5 |
| L9 | 100 PCA7 5 | 95 | | | | | 5.5 |
| L10 | | | 80 | | | 20 | <1.0 |

*Aqueous solution of polymer of an acid group-containing polymerizable monomer in which a portion or the entirety of the acidic group in a molecule forms a salt with an alkaline metal

TABLE 2

| | Composition of Powder material | | | |
|---|---|---|---|---|
| | Acid reactive inorganic powder (c) (wt. %) | | | Silica powder |
| | G1 | G2 | G3 | (wt. %) |
| P1 | | | 100 | |
| P2 | 25 | | 75 | |
| P3 | 50 | | 50 | |
| P4 | 75 | | 25 | |
| P5 | 100 | | | |
| P6 | 75 | 5 | 20 | |
| P7 | 50 | 5 | 45 | |
| P8 | 50 | 25 | 25 | |
| P9 | 50 | 40 | 10 | |
| P10 | 60 | 20 | 20 | |
| P11 | 40 | 60 | | |
| P12 | | | 100 | |
| P13 | 30 | 20 | | 50 |
| P14 | 50 | 30 | | 20 |

TABLE 3

Composition of Examples

| | Liquid material | Powder material | powder/liquid ratio (wt. %) | Liquid material pH | Composition in Cured Product (wt. %) | | | | acid-reactive element-containing |
|---|---|---|---|---|---|---|---|---|---|
| | | | | | (a) Poly acid* | (b) Water | (c) Acid reactive inorganic powder | Other Components | Zinc oxide content in (c) (wt. %) | glass powder content in (c) (wt. %) |
| Example 1 | L1 | P1 | 3.0/1.0 | 4.2 | 5.0 | 20.0 | 75.0 | | | |
| Example 2 | L1 | P2 | 3.0/1.0 | 4.2 | 5.0 | 20.0 | 75.0 | | 25.0 | |
| Example 3 | L1 | P3 | 3.0/1.0 | 4.2 | 5.0 | 20.0 | 75.0 | | 50.0 | |
| Example 4 | L1 | P4 | 3.0/1.0 | 4.2 | 5.0 | 20.0 | 75.0 | | 75.0 | |
| Example 5 | L1 | P5 | 3.0/1.0 | 4.2 | 5.0 | 20.0 | 75.0 | | 100.0 | |
| Example 6 | L1 | P6 | 3.0/1.0 | 4.2 | 5.0 | 20.0 | 75.0 | | 75.0 | 5.0 |
| Example 7 | L1 | P7 | 3.0/1.0 | 4.2 | 5.0 | 20.0 | 75.0 | | 50.0 | 5.0 |
| Example 8 | L1 | P8 | 3.0/1.0 | 4.2 | 5.0 | 20.0 | 75.0 | | 50.0 | 25.0 |
| Example 9 | L1 | P9 | 3.0/1.0 | 4.2 | 5.0 | 20.0 | 75.0 | | 50.0 | 40.0 |
| Example 10 | L1 | P10 | 3.0/1.0 | 4.2 | 5.0 | 20.0 | 75.0 | | 60.0 | 20.0 |
| Example 11 | L1 | P11 | 3.0/1.0 | 4.2 | 5.0 | 20.0 | 75.0 | | 40.0 | 60.0 |
| Example 12 | L1 | P12 | 3.0/1.0 | 4.2 | 5.0 | 20.0 | 75.0 | | | 100.0 |
| Example 13 | L2 | P10 | 3.0/1.0 | 5.5 | 10.0 | 15.0 | 75.0 | | 60.0 | 20.0 |
| Example 14 | L7 | P10 | 3.0/1.0 | 4.2 | 9.5 | 14.25 | 75.0 | 1.25 Tartaric acid | 60.0 | 20.0 |
| Example 15 | L8 | P10 | 3.0/1.0 | 3.5 | 9.5 | 14.25 | 75.0 | 1.25 Phosphoric acid | 60.0 | 20.0 |
| Example 16 | L4 | P10 | 3.0/1.0 | 5.3 | 3.0 | 22.0 | 75.0 | | 60.0 | 20.0 |
| Example 17 | L3 | P10 | 2.0/1.0 | 4.5 | 20.0 | 13.3 | 66.7 | | 60.0 | 20.0 |
| Example 18 | L3 | P10 | 3.0/1.0 | 4.5 | 15.0 | 10.0 | 75.0 | | 60.0 | 20.0 |
| Example 19 | L1 | P10 | 1.5/1.0 | 4.2 | 8.0 | 32.0 | 60.0 | | 60.0 | 20.0 |
| Example 20 | L1 | P10 | 1.0/1.0 | 4.2 | 10.0 | 40.0 | 50.0 | | 60.0 | 20.0 |
| Example 21 | L1 | P10 | 0.8/1.0 | 4.2 | 11.1 | 44.45 | 44.45 | | 60.0 | 20.0 |
| Example 22 | L1 | P10 | 0.5/1.0 | 4.2 | 13.3 | 53.4 | 33.3 | | 60.0 | 20.0 |
| Example 23 | L4 | P10 | 0.5/1.0 | 5.3 | 8.0 | 58.7 | 33.3 | | 60.0 | 20.0 |
| Example 24 | L1 | P10 | 5.0/1.0 | 4.2 | 3.3 | 13.3 | 83.4 | | 60.0 | 20.0 |

*Polymer of an acid group-containing polymerizable monomer in which a portion or the entirety of the acidic group in a molecule forms a salt with an alkaline metal

TABLE 4

Composition of Comparative Examples

| | Liquid material | Powder material | powder/liquid ratio (wt. %) | Liquid material pH | (a) Poly acid* | (b) Water | (c) Acid reactive inorganic powder | Silica powder | Other Components | Zinc oxide content in (c) (wt. %) | acid-reactive element-containing glass powder content in (c) (wt. %) |
|---|---|---|---|---|---|---|---|---|---|---|---|
| Comparative Example 1 | L1 | P13 | 1.0/1.0 | 4.2 | 10.0 | 40.0 | 25.0 | 25.0 | | 60.0 | 40.0 |
| Comparative Example 2 | L3 | P10 | 1.4/1.0 | 4.5 | 25.0 | 16.7 | 58.3 | | | 60.0 | 20.0 |
| Comparative Example 3 | L9 | P10 | 3.0/1.0 | 5.5 | 1.25 | 23.75 | 75.0 | | | 60.0 | 20.0 |
| Comparative Example 4 | L5 | P10 | 3.0/1.0 | 3.0 | 10.0 | 15.0 | 75.0 | | | 60.0 | 20.0 |
| Comparative Example 5 | L6 | P10 | 3.0/1.0 | 6.2 | 5.0 | 20.0 | 75.0 | | | 60.0 | 20.0 |
| Comparative Example 6 | L3 | P10 | 4.5/1.0 | 4.5 | 10.9 | 7.3 | 81.8 | | | 60.0 | 20.0 |
| Comparative Example 7 | L9 | P10 | 0.5/1.0 | 5.5 | 3.3 | 63.4 | 33.3 | | | 60.0 | 20.0 |
| Comparative Example 8 | L10 | P14 | 3.0/1.0 | <1.0 | | 20.0 | 60.0 | 15.0 | 5.0 PAA | 62.5 | 37.5 |
| Comparative Example 9 | | | | | Product A (CANALS/SHOWA YAKUHIN KAKO CO., LTD.) | | | | | | |
| Comparative Example 10 | | | | | Product B (CANALS-N/SHOWA YAKUHIN KAKO CO., LTD.) | | | | | | |
| Comparative Example 11 | | | | | Product C (Sankin apatite root sealer type I/DENTSPLY-Sankin KK.) | | | | | | |
| Comparative Example 12 | | | | | Product D (Super bond root filling sealer/Sun Medical Co., Ltd.) | | | | | | |

* Polymer of an acid group-containing polymerizable monomer in which a portion or the entirety of the acidic group in a molecule forms a salt with an alkaline metal

TABLE 5

Evaluation Result

| | Odor | Kneaded material pH | Operation surplus time (Minute) | Curing time (Minute) | Compressive strength (MPa) | Removability |
|---|---|---|---|---|---|---|
| Example 1 | A | 5.4 | 16 | 150 | 9.2 | A |
| Example 2 | A | 5.4 | 16 | 160 | 8.6 | A |
| Example 3 | A | 5.5 | 17 | 180 | 6.1 | AA |
| Example 4 | A | 5.4 | 18 | 180 | 6.4 | AA |
| Example 5 | A | 5.5 | 20 | 210 | 5.9 | AA |
| Example 6 | A | 6.1 | 16 | 180 | 6.2 | AA |
| Example 7 | A | 6.1 | 16 | 170 | 6.2 | AA |
| Example 8 | A | 6.3 | 14 | 130 | 6.0 | AA |
| Example 9 | A | 6.5 | 13 | 120 | 6.5 | AA |
| Example 10 | A | 6.3 | 15 | 130 | 5.8 | AA |
| Example 11 | A | 6.7 | 11 | 100 | 8.4 | A |
| Example 12 | A | 6.9 | 10 | 60 | 11.3 | A |
| Example 13 | A | 6.5 | 18 | 160 | 5.4 | AA |
| Example 14 | A | 6.2 | 16 | 140 | 5.5 | AA |
| Example 15 | A | 5.9 | 16 | 130 | 5.7 | AA |
| Example 16 | A | 6.6 | 16 | 130 | 6.0 | AA |
| Example 17 | A | 6.4 | 12 | 110 | 7.1 | AA |
| Example 18 | A | 6.5 | 13 | 120 | 6.8 | AA |
| Example 19 | A | 6.2 | 16 | 130 | 6.1 | AA |
| Example 20 | A | 6.3 | 16 | 140 | 6.0 | AA |
| Example 21 | A | 6.4 | 17 | 160 | 5.9 | AA |
| Example 22 | A | 6.5 | 18 | 170 | 5.7 | AA |
| Example 23 | A | 6.6 | 18 | 180 | 5.4 | AA |
| Example 24 | A | 6.5 | 12 | 100 | 7.3 | AA |
| Comparative Example 1 | A | 5.4 | 20 | 240 | 2.2 | AA |
| Comparative Example 2 | A | 6.3 | 8 | 80 | 8.3 | A |

TABLE 5-continued

| | Odor | Kneaded material pH | Operation surplus time (Minute) | Curing time (Minute) | Compressive strength (MPa) | Removability |
|---|---|---|---|---|---|---|
| Comparative Example 3 | A | 6.5 | 19 | 180 | 2.1 | AA |
| Comparative Example 4 | B | 4.1 | 7 | 90 | 15.6 | B |
| Comparative Example 5 | A | 7.2 | >30 | >300 | 1.3 | AA |
| Comparative Example 6 | A | 6.3 | 7 | 90 | 18.1 | B |
| Comparative Example 7 | A | 6.2 | 22 | 210 | 1.6 | AA |
| Comparative Example 8 | C | 3.1 | 3 | 8 | 6.7 | AA |
| Comparative Example 9 (Product A) | C | unmeasurable | >30 | >300 | 6.7 | AA |
| Comparative Example 10 (Product B) | C | unmeasurable | >30 | >300 | unmeasurable | AA |
| Comparative Example 11 (Product C) | B | 3.5 | 6 | 90 | 9.4 | A |
| Comparative Example 12 (Product D) | C | unmeasurable | 5 | 45 | >400 | C |

Examples 1 to 241

The sealer compositions for root canal filling of Examples 1 to 24 had no odor and the pH of the kneaded materials were high. Further, these sealer compositions for root canal filling had a sufficient operation surplus time suitable for root canal filling and the moderately low compressive strength, and was excellent to removability. In particular, the sealer compositions for root canal filling of Examples 3 to 10 and Examples 13 to 24 had the moderately low mechanical strength and were very excellent to removability because the content of zinc oxide was more than 50 part by weight in the acid reactive inorganic powder (c). Among these, in the sealer compositions for root canal filling of Examples 6 to 10 and Examples 13 to 24, the pH of the kneaded material rapidly transfer to a neutral because the content of the acid-reactive element-containing glass powder is in the range from 5 to 40 part by weight in the acid reactive inorganic powder (c).

Comparative Example 1

The sealer composition for root canal filling of Comparative Example 1 did not satisfy the requirements of the present disclosure because the content of the acid reactive inorganic powder (c) in the cured product was less than 30 part by weight. As a result, because the mechanical strength of the cured product was too low, there was concern about the lack of durability in the sealer composition for root canal filling of Comparative Example 1.

Comparative Example 2

The sealer composition for root canal filling of Comparative Example 2 did not satisfy the requirements of the present disclosure because the content of the polymer (a) of an acid group-containing polymerizable monomer in which a portion or the entirety of the acidic group in a molecule forms a salt with an alkaline metal in the cured product was more than 20 part by weight. As a result, because the curing rate became faster, the sealer composition for root canal filling of Comparative Example 2 did not have a sufficient operation surplus time suitable for root canal filling.

Comparative Example 3

The sealer composition for root canal filling of Comparative Example 3 did not satisfy the requirements of the present disclosure because the content of the polymer (a) of an acid group-containing polymerizable monomer in which a portion or the entirety of the acidic group in a molecule forms a salt with an alkaline metal in the cured product is less than 3 part by weight. As a result, because the mechanical strength of the cured product was too low, there was concern about the lack of durability in the sealer composition for root canal filling of Comparative Example 3.

Comparative Example 4

The sealer composition for root canal filling of Comparative Example 4 did not satisfy the requirements of the present disclosure because the pH of the liquid material was less than 3.5. As a result, the sealer composition for root canal filling of Comparative Example 4 had an odor, the pH of the kneaded material was low. Further, because the curing rate became faster, the sealer composition for root canal filling of Comparative Example 4 did not have a sufficient operation surplus time suitable for root canal filling. Further, the mechanical strength of the cured product became too high and removability was poor.

Comparative Example 5

The sealer composition for root canal filling of Comparative Example 5 did not satisfy the requirements of the present disclosure because the pH of the liquid material was more than 5.5. As a result, because the mechanical strength of the cured product was too low, there was concern about the lack of durability in the sealer composition for root canal filling of Comparative Example 5.

Comparative Example 6

The sealer composition for root canal filling of Comparative Example 6 did not satisfy the requirements of the present disclosure because the content of the water (b) in the cured product was lower than 10 part by weight. As a result, because the curing rate became faster, the sealer composition for root canal filling of Comparative Example 6 did not have a sufficient operation surplus time suitable for root canal filling. Further, the mechanical strength of the cured product became too high and removability was poor.

Comparative Example 7

The sealer composition for root canal filling of Comparative Example 7 did not satisfy the requirements of the present disclosure because the content of the water (b) in the cured product was more than 60 part by weight. As a result, because the mechanical strength of the cured product was too low, there was concern about the lack of durability in the sealer composition for root canal filling of Comparative Example 7.

Comparative Example 8

The sealer composition for root canal filling of Comparative Example 8 did not contain the polymer (a) of an acid group-containing polymerizable monomer in which a portion or the entirety of the acidic group in a molecule forms a salt with an alkaline metal, which is the requirement of the present disclosure, but contained an acrylic acid homopolymer powder (a polymer of an acid group-containing polymerizable monomer) instead. Further, the pH of the liquid material was lower than 3.5. Therefore, the sealer composition for root canal filling of Comparative Example 8 did not satisfy the requirements of the present disclosure. As a result, the sealer composition for root canal filling of Comparative Example 8 had a strong odor, and the pH of the kneaded material was low. Further, because the curing rate became faster, the sealer composition for root canal filling of Comparative Example 8 did not have a sufficient operation surplus time suitable for root canal filling.

Comparative Example 9

The sealer composition for root canal filling of Comparative Example 9 is a commercially available zinc oxide-eugenol based sealer for root canal filling (CANALS/SHOWA YAKUHIN KAKO CO., LTD.). As a result of the test, the sealer composition for root canal filling of Comparative Example 9 had a strong unpleasant odor peculiar to eugenol.

Comparative Example 10

The sealer composition for root canal filling of Comparative Example 10 is a commercially available fatty acid based sealer for root canal filling (CANALS-N/SHOWA YAKUHIN KAKO CO., LTD.). As a result of the test, the sealer composition for root canal filling of Comparative Example 10 had an odor peculiar to fatty acid.

Comparative Example 11

The sealer composition for root canal filling of Comparative Example 11 is a commercially available calcium phosphate/apatite based sealer for root canal filling (Sankin apatite root sealer type I/DENTSPLY-Sankin K.K.). As a result of the test, the sealer composition for root canal filling of Comparative Example 11 had an odor, the pH of the kneaded material thereof was low. Further, the sealer composition for root canal filling of Comparative Example 11 did not have a sufficient operation surplus time suitable for root canal filling.

Comparative Example 12

The sealer composition for root canal filling of Comparative Example 12 is a commercially available resin-based sealer for root canal filling (Super bond root filling sealer/Sun Medical Co., Ltd.). As a result of the test, the sealer composition for root canal filling of Comparative Example 12 had an odor peculiar to resin, did not have a sufficient operation surplus time suitable for root canal filling. Further, the mechanical strength of the cured product became too high and removability was poor.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

What is claimed is:

1. A sealer composition for root canal filling, wherein, the sealer composition for root canal filling consisting of;
    a liquid material containing a polymer (a) of an acid group-containing polymerizable monomer in which a portion or the entirety of the acidic group in a molecule forms a salt with an alkaline metal and water (b), wherein the pH of the liquid material is in the range from 3.5 to 5.5, and
    a powder material containing an acid reactive inorganic powder (c), wherein,
    a cured product of a kneaded material of the liquid material and the powder material comprises 3 to 20 part by weight of the polymer (a) of an acid group-containing polymerizable monomer in which a portion or the entirety of the acidic group in a molecule forms a salt with an alkaline metal, 10 to 60 part by weight of the water (b), and 30 to 85 part by weight of the acid reactive inorganic powder (c), and
    the acid reactive inorganic powder (c) contains zinc oxide, and 5 to 40 part by weight of an acid-reactive element-containing glass powder for the whole amount of the acid reactive inorganic powder (c).

2. The sealer composition for root canal filling according to claim 1, wherein,
    the polymer (a) of an acid group-containing polymerizable monomer in which a portion or the entirety of the acidic group in a molecule forms a salt with an alkaline metal is a polymer of α-β unsaturated carboxylic acid in which a portion or the entirety of the acidic group in a molecule forms a salt with an alkaline metal.

3. The sealer composition for root canal filling according to claim 1, wherein,
    an operation surplus time at 23° C. is 10 minutes or more.

4. The sealer composition for root canal filling according to claim 2, wherein,
    an operation surplus time at 23° C. is 10 minutes or more.

* * * * *